United States Patent [19]

Mohammed

[11] 4,270,905

[45] Jun. 2, 1981

[54] REPLACEMENT SYSTEM FOR DENTAL AND OTHER BONE IMPLANTS

[76] Inventor: M. Hamdi A. Mohammed, 3236 SW. 62nd La., Gainesville, Fla. 32601

[21] Appl. No.: 13,064

[22] Filed: Feb. 21, 1979

[51] Int. Cl.³ .............................................. A61C 8/00
[52] U.S. Cl. ................................... 433/201; 433/173
[58] Field of Search ............... 433/201, 173, 174, 175, 433/176

[56] References Cited

U.S. PATENT DOCUMENTS

| | | | |
|---|---|---|---|
| 3,707,006 | 12/1972 | Bokros et al. | 433/201 |
| 3,863,344 | 2/1975 | Pillet | 433/175 |
| 3,934,347 | 1/1976 | Lash et al. | 433/201 |
| 3,955,280 | 5/1976 | Sneer | 433/174 |
| 3,971,134 | 7/1976 | Bokros | 433/201 |
| 4,081,908 | 4/1978 | Sneer | 433/173 |

Primary Examiner—Gene Mancene
Assistant Examiner—John J. Wilson
Attorney, Agent, or Firm—Prutzman, Kalb, Chilton & Alix

[57] ABSTRACT

A dental implant system to provide a mechanically self-sufficient artificial tooth possessing a functional pseudo peridontal ligament that does not cause resorption of the supporting bone and ultimate loss is disclosed. The implant includes a core component that withstands the masticatory load and transmits such load to the root system. The root system comprises an outer component that adheres to the jawbone and possesses a similar modulus of elasticity thus capable of transmitting masticatory stresses along its interface with the bone without excessive stress concentrations and an intermediate component adhering tightly to both the core component and the outer component and having a much lower modulus of elasticity than either the core component and the outer component. The longitudinal movement of the core component causes the oblique or diagonal stretching of the intermediate component which pulls or applies a force on the outer component which tends to contract it and creates tensile stresses in the portions of the supporting jawbone which interface with the outer component. Such tensile stresses cause bone deposition and stabilize the implant further.

9 Claims, 1 Drawing Figure

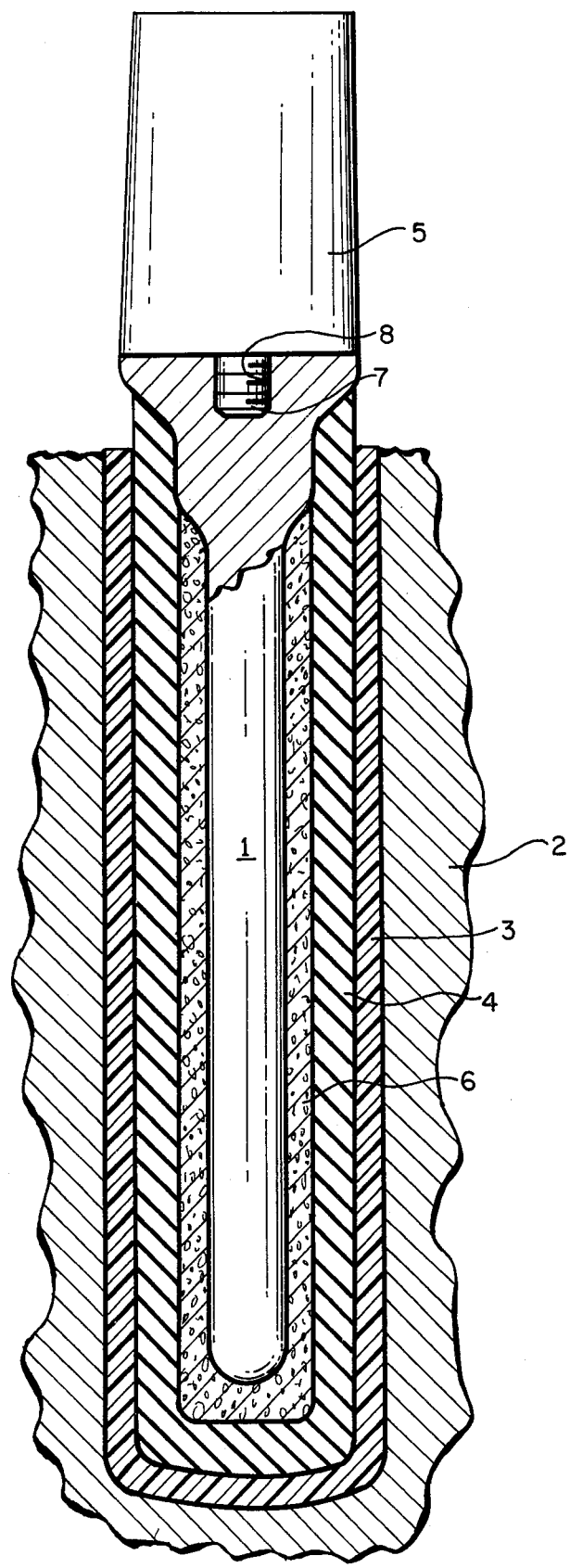

REPLACEMENT SYSTEM FOR DENTAL AND OTHER BONE IMPLANTS

This invention relates to the development of a replacement tooth system that can be successfully used as a bone anchorage and is particularly useful as a permanent mechanically self-sufficient dental implant replacing a lost natural single tooth.

Specifically, this invention introduces a replacement system such as a dental implant uniquely designed to induce tensile stresses in the surrounding bone to enhance its survival in the same manner a natural tooth does when under a biting load. In this manner, the replacement system is permanent and functions in a healthy physiologic manner in contrast to current implants which characteristically induce pathologic compressive stresses in and subsequent resorption of the surrounding bone.

Although dental implants that replace single teeth are available, the clinical success ratio of these implants suggests the current absence of any dental implant that truly functions in a self-sustaining and permanent manner similar to a natural tooth.

In dentistry, the subject of introducing a dental implant has received a great deal of attention. Attempts at implanting teeth through the insertion of metallic, ceramic, or polymeric devices that looked like a tooth into sugically prepared sockets in the jaw bone have been made. Invariably such devices were initially splinted to neighboring natural teeth by wires or crowns and were relieved from carrying any masticatory load for a period of time. After a few months, the device appeared to have healed and stabilized, and the splinting was removed to permit the implant to be self-supporting and a crown was installed on the coronal portion of the implant so that it would carry its share of the masticatory load. Most often, the bone surrounding the implant was resorbed gradually and the implant loosened resulting in complete loss or removal.

The implant loss has been attributed to the lack of tissue compatibility of the implant material and was thought to be a mere process of tissue rejection of foreign bodies. Using materials proven over many years to be compatible with the human tissues did not alleviate the failures, however.

A second reason advanced as the cause of bone resorption around an implant was that roughness of the implant at the point of its entry into the tissues or at its neck or cervical portion caused a chronic inflamation of the gum tissue which in turn caused the progressive resorption of the underlying bone. Efforts to introduce extremely dense and glass-polished implant neck alleviated the inflamation of the gum but did not reduce the resorption of bone, however.

A third reason advanced as the cause of bone resorption was that the shape or design of the root portion of the implant caused concentrations of excessive stresses at isolated points which in turn triggered the bone resorption. Countless designs of dental implants have been introduced in various shapes, thickness, size and materials. Such efforts have not reduced the rate of progressive bone resorption.

A fourth reason thought to be responsible for bone resorption around the implant has been considered more recently. Most implants are made from materials which possess a modulus of rigidity (modulus of elasticity) much higher or much lower than that of the surrounding bone. The rigidity of metallic materials is 5 to 10 times greater, that of ceramic materials is 15 to 20 times greater, and that of polymeric materials is 0.1 to 0.2 times as much as that of bone. As such, when a metallic implant, for example, is inserted in bone, the stresses generated from the loading of mastication propagate through the metallic implant towards its periphery but there is a sharp discontinuity of the transmission at the interface of the metal and the surrounding bone. Such lack of continuity of stress transmittal is due to the severe and sudden differential in the modulus of elasticity between metal of the implant and the bone. In this event, severe stresses are concentrated at the interface between the implant and the bone. Similar stress concentrations occur when a ceramic or a polymeric material is used. Such severe stresses cause bone resorption, loosening and ultimate loss of the implant. Such reasoning has led to the consideration of the use of either materials possessing a modulus or elasticity close to that of bone for the construction of dental implants or to the coating of the metallic implants with such materials. A tissue compatible material that possesses a modulus of elasticity similar to that of bone is carbon. Implants made from vitreous or pyrolytic carbon as well as metallic implants coated with pyrolytic carbon have been tried. Such efforts have reduced the rate of implant loss due to bone resorption somewhat but did not eliminate such losses. This is because even though the continuity in stress transmittal from implant to bone was achieved through the use of materials possessing a similar modulus of elasticity to that of bone, the stresses transmitted into the bone due to loading on the implant were still compressive in nature. Compressive stresses are well known to cause bone resorption even in their slightest magnitude. Suffice to state that the application of minor stresses as low as one kilogram per square centimeter on a healthy tooth for a period of time causes bone resorption and hence tooth movement in the direction of bone resorption. This principle is the one underlying orthodontic movement of natural teeth which has been successfully used to straighten teeth for generations.

In contrast to all the above implant designs, loading of a natural tooth generates tensile stresses in the bone surrounding it and enhances bone deposition if such deposition is necessary, but more importantly, inhibits any resorption if such bone deposition is not necessary. As such, the natural tooth is designed in a manner similar to that of a muscle so that the more it is used the stronger and the more stable it becomes. As such, the natural tooth is designed to be self-sustaining and its support mechanism is permanent.

It is a primary object of this invention to provide a replacement system for dental and other bone implants that dynamically functions in a manner similar to that of the natural tooth.

Another object of this invention is to provide a dental implant design that induces tensile stresses in the supporting bone.

A still further object of this invention is to introduce a three component dental implant system.

Another object of this invention is to provide a three-component dental implant system which functions in a manner corresponding to that of a natural tooth.

A still further object of this invention is to provide a dental implant device that replaces the whole lost tooth system rather than just replacing the tooth itself.

Still another object of this invention is the provision of a dental implant device consisting of a rigid core equalling the rigidity of the tooth, a relatively soft layer surrounding the core, and a third layer possessing rigidity similar to that of bone.

A further object of this invention is the provision of a dental implant device core that, when loaded by the masticatory load in compression, will move apically pulling onto the relatively soft layer surrounding the root portion of the core which in turn pulls onto the outer most layer possessing a modulus of elasticity similar to that of bone thus inducing tensile stresses in the supporting jaw bone to enhance its stability.

Other objects will be in part obvious and in part pointed out more in detail hereinafter.

The invention accordingly comprises the combination of materials disclosed herein and articles possessing the design combination, features, properties, and characteristics which are exemplified in the following disclosure.

In the drawing, the single FIGURE is a schematic illustration of the three component artifical dental implant device embodying my invention.

In order to attain a self-sufficient and permanent dental implant system, the system must firstly be capable of withstanding the compressive masticatory load and of such rigidity to transmit such load along the longitudinal axis of the system. Core 1 performs this function.

A second mandatory feature of the dental implant system embodying this invention is that the root portion in contact with the jawbone 2 must have a modulus of elasticity similar to that of bone. Component 3 of the dental implant system of this invention referred to hereinafter as the outer component, performs this function. A third mandatory feature of the dental implant system of this invention and the one playing the vital role is an intermediate component 4 that permits the apical motion of the core component and at the same time pulls onto the outer component 3 to generate tensile stresses in the supporting bone. The intermediate component 4 must possess a modulus of elasticity much lower than that of either the core component or the outer component. Preferably its modulus of elasticity should be one-fifth as much or less.

In addition to the above three mandatory features, the core 1 must be provided with means to securely attach it to the relatively soft intermediate component 4. Further, the outer component 3 must also be securely attached to the intermediate component and to the bone 2. In addition, the dental implant system must be provided with a coronal portion 5 ready to receive a dental crown (not shown). Such a coronal component may, as shown, be formed separate from the core 1 and firmly secured thereto by threaded connection 7, 8 and must be of adequate rigidity and density that permits the support of the dental crown. Further, the point of junction between the coronal portion 5 and the root system of the implant system must be of sufficient density and polish to assure the absence of any irritation to the surrounding gum tissue.

In addition to all the above requirements, all components of the implant system exposed to the oral cavity environment must be non-corrosive and non-irritating to all oral tissues.

Preferably the outer periphery of the outer component 3 should be generally cylindrical in cross section or slightly tapering towards the apex to permit the greatest surface area for load transmittal. The apex is preferably semicircular rather than pointed or flat to permit even distribution of apical stresses without excessive concentration. Since a cylindrical root geometry will not permit adequate resistance to rotation due to tipping and lateral masticatory loads, the essentially cylindrical surface of the outer component is preferably undulated. Such undulations also assist in resisting occlusal masticatory forces attempting to displace the whole implant system apically. Slight apical displacement of the core 1 and the intermediate component 4 will take place relative to the outer component 3 but apical displacement of the outer component must not take place. Should apical displacement of the outer component 3 take place, the conversion of compressive masticatory forces at the occlusal surface of the implant system to tensile stresses into the supporting alveolar bone will not occur and pathologic compressive stresses, similar to those generated by currently available dental implants, will occur in the supporting jaw bone causing its resorption.

Core 1 should consist of a dense material having a high modulus of elasticity. The core 1 consists of the prepared coronal portion or coping and a dense shaft extending through the center of the root system. Both coping and shaft may be processed from a metal alloy suitable for implant purposes, a ceramic, or a high density high rigidity polymeric material. Graphite or high density pyrolytic carbon may also be utilized.

The shaft of the core 1 must be fixedly secured to intermediate component 4 and preferably is provided with a layer 6 of porous material tightly adhered to the shaft. Porous layer 6 may be made of powdered metals, porous ceramics, or a porous but rigid polymeric material which is compatible with the shaft of the core component 1. Preferably, the core 1 is cast from a surgical implant alloy such as chromium cobalt, titanium, or 316 stainless steel, and the porous layer 6 is formed on the surface of the shaft by sintering the powdered layer to the shaft. The occlusal extent of the porous layer 6 of the core component should be well below the occlusal extent of the outer component 3 as clearly depicted in the figure.

The intermediate component 4 consists of a biologically compatible material possessing a modulus of elasticity well below that of the core component 1 and that of the outer component 3. The intermediate component 4 may be processed from a low modulus polymeric material such as polymethyl methacrylate, from a low modulus pyrolytic carbon deposit, or from a surgical silicone rubber of high molecular weight. Preferably, a polymethylmethacrylate polymer is used. This polymer can flow easily into the voids of porous layer 6 to be mechanically interlocked therewith and form the required adherence and is compatible with human tissues. Another advantage for this polymer is its thermoplastic nature which furnishes an alternate mechanism for its placement via heat forming. It should be noted that the intermediate component 4 should extend occlusally above both of the core 1 and the outer component 3 and its exposed cervical portion must be extremely dense and of high polish or smoothness. The remaining portion of the intermediate component 4 and the adjoining surfaces of core 1 and outer component 3 may be porous, undulated or sinusoidal to facilitate the tight adherence therebetween.

Outer component 3 must be formed from a material possessing a modulus of elasticity close to that of bone possessing a modulus of elasticity close to that of bone and the ratio of the modulus of elasticity of outer component 3 to that of bone should not be smaller than 0.5 or greater than 2.0. Should the ratio of the modulus of elasticity of outer component 3 to that of bone deviate from the above range that was found most suitable, stresses will concentrate at the outer component bone-interface leading to bone resorption. Excessive stress concentration, even if the stresses were tensile in nature, due to severe differentials in the moduli of elasticity of the outer component 3 and of bone is also believed to cause bone resorption. The modulus of outer component 3 must range from one to four million pounds per square inch, and outer component 3 must be processed from materials possessing such moduli. A high molecular weight polymer, graphite, prolytic carbon, and bioglass are found to possess such moduli of elasticity. Since the outer component must be firmly adhered to bone 2 after healing, the material for its construction must be of high tissue compatibility. The material must also be capable of either being processed in a porous condition such as in the case of pyrolytic carbon or must be capable of adhereing chemically (ankylose) to the bone such as in the case of bioglass. Preferably, outer component 3 will be formed of porous pyrolytic carbon deposit which is highly compatible with human tissues, possesses a modulus of elasticity of three to four million pounds per square inch and can be easily deposited in the porous condition. As such, bone will grow into the pores of the pyrolytic carbon of the outer component 3 and tightly hold the whole implant root system in position. The outer component should extend occlusally well beyond porous layer 6 of core 1.

As an alternative, core 1 may be machined or cast from a titanium alloy. A powdered titanium layer 6 may then be placed around the core's shaft and sintered. A porous pyrolytic carbon jacket 3 of the appropriate size may then be separately prepared. The pyrolytic carbon jacket may then be lined with a mixture of either heat curing or self curing polymethylmethacrylate and the core 1 inserted into the jacket and the polymer then polymerized to form the intermediate component 4 and firmly adhere it to core 1 and the outer jacket or component 3. The cervical portion may then be polished to a high luster. After the implant is sterilized it is now ready for insertion into a prepared recess in the jawbone. Once inserted, the bone grows into the pores of the pyrolytic carbon outer layer 3. The polymethylmethacrylate intermediate component 4 fills the annular gap between the core 1 and the outer component 3.

Once healing is complete, a crown may be cemented to the coronal portion 5 of the implant to complete the dental procedure of installing the implant.

As the patient bites on the occlusal surface of the implant, the compressive biting forces move the core component slightly in an apical direction. Such apical motion of the core causes oblique or diagonal stretching of the polymethylmethacrylate of the intermediate component 4 between the core 1 and the outer component 3. This in turn pulls or applies a contraction force tending to contract the outer component 3. Since outer layer 3 is tightly held to the jawbone 2, tensile stresses are generated into the interface portions of bone enhancing bone deposition. In such a manner, the implant maintains its permanent support by the jawbone 2.

The shaft of the core 1 will normally be approximately 1 millimeter in diameter, but it will be understood that the size will depend upon the width and depth of the jawbone location where it is to be used.

From the foregoing, it is readily apparent that the dental implant system of this invention provides the design and functionality necessary for a permanent and mechanically self-sufficient artificial tooth.

As will be apparent to persons skilled in the art, various modifications of the above described invention will become readily apparent without departure from the spirit and scope of the invention.

I claim:

1. A tooth replacement system comprising a dental implant having a core providing a central shaft having a lower end, an outer component adapted to be positioned in a socket in the jawbone surrounding the central shaft and spaced therefrom to define a gap therewith, an intermediate component disposed in the gap, and means securing the intermediate component both to the central shaft and to the surrounding wall of the outer component, the intermediate component having a lower modulus of elasticity than either the central shaft or the outer component to permit axial movement of the central shaft relative to the outer component, said outer component having a modulus of elasticity which approximates that of bone, said central shaft being non-convergent toward its lower end so that axial movement of the central shaft relative to the outer component imparts tensile stresses in said intermediate component which tend to contract said outer component thereby to impart tensile stresses in the surrounding portions of the supporting jawbone.

2. The tooth replacement system of claim 1 wherein the modulus of elasticity of the intermediate layer is no more than about one-fifth as much as that of either the central shaft of the outer layer.

3. The tooth replacement system of claim 1 wherein the central shaft has a porous surface layer adjacent the gap and the intermediate component is engaged in the voids thereof.

4. The tooth replacement system of claim 3 wherein the outer component has a porous surface layer adjacent the gap and the intermediate component is engaged in the voids thereof.

5. The tooth replacement system of claim 1 wherein the outer component has an outer surface which is porous to permit bone growth therein.

6. The tooth replacement system of claim 1 wherein the modulus of elasticity of the outer component is in the range of about 0.5–2 times that of bone.

7. A bone implant having a core providing a central shaft having a lower end, an outer component adapted to be positioned in a socket formed in a bone surrounding the central shaft and spaced therefrom to define a gap therewith, an intermediate component disposed in the gap, and means securing the intermediate component both to the central shaft and to the surrounding wall of the outer component, the outer component having a modulus of elasticity approximately that of bone, the intermediate component having a lower modulus of elasticity than either the central shaft or the outer component to permit axial movement of the central shaft relative to the outer component, said central shaft being non-convergent toward its lower end so that axial movement of the central shaft relative to the outer component imparts tensile stresses in said intermediate component which tend to contract said outer component thereby to impart tensile stresses in the surrounding portions of the supporting bone.

8. The bone implant of claim 7 wherein the modulus of elasticity of the outer component is in the range of about 0.5–2 times that of bone.

9. The bone implant of claim 7 wherein the outer component is porous to permit bone growth therein.

* * * * *